United States Patent [19]

Olins

[11] Patent Number: 4,740,499

[45] Date of Patent: Apr. 26, 1988

[54] METHOD OF ENHANCING THE BIOACTIVITY OF ATRIAL PEPTIDES

[75] Inventor: Gillian M. Olins, Ballwin, Mo.

[73] Assignee: Monsanto Company, St. Louis, Mo.

[21] Appl. No.: 889,670

[22] Filed: Jul. 28, 1986

[51] Int. Cl.$^4$ .............................................. A61K 37/02
[52] U.S. Cl. ...................................................... 514/13
[58] Field of Search .......................................... 514/13

[56] References Cited

U.S. PATENT DOCUMENTS 4,496,544 1/1985 Needleman ............................ 514/13
4,513,099 4/1985 Roques et al. ...................... 514/513

FOREIGN PATENT DOCUMENTS 82088 6/1983 European Pat. Off. .

OTHER PUBLICATIONS

Burnett et al., Am. J. Physiol. 247, F863-6 (1984).
Luft et al., J. Pharmacol. Exp. Ther. 236(2), 416-418 (1986).
Yandle et al., Life Sci. 38, 1827-1833 (1986).
Briggs et al., Chem. Absts. 101:184852 (1984).
Thibault et al., Chem. Absts. 101: 66823 (1984).
Tang et al., Chem. Absts. 102:1084 (1985).
Roques et al., Nature 288, 286-288 (1980).
Bouboutou et al., Life Sci. 35, 1023-30 (1984).
Fournié-Zaluski et al., J. Med. Chem. 28, 1158-69 (1985).
Kenny et al., Biochem. Soc. Trans. 13, 293-295 (1985).
Fulcher et al., Biochem. J. 203, 519-522 (1984).
Chemical Abstracts, vol. 105, No. 146991.

*Primary Examiner*—Delbert R. Phillips
*Attorney, Agent, or Firm*—Scott J. Meyer; James W. Williams, Jr.

[57] ABSTRACT

A method of prolonging or enhancing the bioactivity of atrial peptides is disclosed in which thiorphan or kelatorphan is administered contemporaneously with the administration of the atrial peptide.

5 Claims, No Drawings

METHOD OF ENHANCING THE BIOACTIVITY OF ATRIAL PEPTIDES

BACKGROUND OF THE INVENTION

This invention relates to atrial peptides and more particularly to a method of prolonging or enhancing the biological activity of atrial peptides.

In recent years, considerable research investigation has been made on the atrial peptides. These are polypeptide hormones which were originally extracted from the heart atrial muscle. They have been denoted by various terminology such as cardionatrin, atrial natriuretic factor (ANF), atriopeptin (AP), atriopeptigen and auriculin. Biological activity has been shown with these peptides having amino acid chain lengths from as short as about 18 amino acids to as long as over 100 amino acids. The biological activity includes diuretic, natriuretic, smooth muscle relaxing, blood pressure lowering and other such properties having an important role in the regulation of volume balance, sodium homeotasis and vascular tone.

A great number of detailed articles have been published on the structure and biological properties of various of the atrial peptides. For brief background information on the atrial peptides in general, reference can be made to the following recent publications and the references cited therein:

Sagnella and MacGregor, Nature 309, 666–667 (1984);
Palluk et al., Life Sci. 36(15), 1415–1425 (1985);
Needleman et al., Hypertension 7(4), 469–482 (1985);
de Bold, Science 230, 767–770 (1985); and
Needleman and Greenwald, N. Eng. J. Med. 314(13), 828–834 (1986).

An important group of atrial peptides of significant interest, known as Atriopeptins I, II and III (AP-I, AP-II and AP-III), are described, for example, by Currie et al. Science 223, 67–69 (1984); Geller et al., Biochem. Biophys. Res. Commun. 120(2), 333–338 (1984); and Needleman, U.S. Pat. No. 4,496,544. These peptides in the oxidized (cyclized) form have the following amino acid sequences:

for ile[12] is described by Kangawa and Matsuo, Biochem. Biophys. Res. Commun. 118(1), 131–139 (1984).

The 26 amino acid peptide arg-arg-AP-III, also known as atrial natriuretic factor or ANF (8-33), is disclosed as a fragment of a larger 33 amino acid peptide by Seidah et al., Proc. Nat. Acad. Sci. USA 81, 2640–44 (1984).

The 25 amino acid analog of AP-III having an arg extension at the amino acid terminus, also known as auriculin, is described by Yamanaka et al., Nature 309, 719–22 (1984).

The relationship of the foregoing small peptides to a common precursor is illustrated by Sagnella and MacGregor, Nature 309, 666–667 (1984).

As reported in the literature, these small atrial peptides have been shown to have potent diuretic activity upon intravenous administration. For example, such effects have been shown in the dog at 10–30 μg/kg i.v. and at 100 μg i.v. bolus in humans.

Despite the useful biological activity of the atrial peptides, it has been reported that they have a relatively short half-life. See, for example, Burnett et al., Am. J. Physiol. 247, F863–F866 (1984); Luft et al., J. Pharmacol. Exp. Ther. 236(2), 416–418 (1986); and Yandle et al., Life Sci. 38, 1827–1833 (1986). It has also been suggested that proteolytic degradation causes relatively rapid loss of the atrial peptide bioactivity. For example, inactivation of atrial peptide by renal kallikrein was described by Briggs et al., Am. J. Physiol. 247 (3, Pt. 2), F480–F484 (1984); and Thibault et al., Can. J. Physiol. Pharmacol. 62(6), 645–649 (1984). Proteolytic degradation of atrial peptide by kidney and liver homogenates has been described by Tang et al., Regul. Pept. 9(1–2), 53–9(1984).

Harris et al., Peptides (Fayettsville, N.Y.) 6(3), 393–396 (1985), reported that AP-II is converted to AP-I by a bovine atrial enzyme, namely, atrial dipeptidyl carboxhydrolase, which is a metalloenzyme. This does not, however, constitute inactivation but conversion from one active form of the atrial peptide to another during processing.

Methods of prolonging or enhancing the bioactivity

ATRIOPEPTIN I
1
Ser—ser—cys—phe—gly—gly—arg—ile—asp—arg—ile—gly—ala—gln—ser—gly—
           |                                                      21
leu—gly—cys—asn—ser ATRIOPEPTIN II
1
Ser—ser—cys—phe—gly—gly—arg—ile—asp—arg—ile—gly—ala—gln—ser—gly—
           |                                                      23
leu—gly—cys—asn—ser—phe—arg ATRIOPEPTIN III
1
Ser—ser—cys—phe—gly—gly—arg—ile—asp—arg—ile—gly—ala—gln—ser—gly—
           |                                                      24
leu—gly—cys—asn—ser—phe—arg—tyr Extensions of AP-III have also been described. Thus, the 28 amino acid peptide ser-leu-arg-arg-AP-III (SLRR-AP-III), also known as Cardionatrin I, is disclosed in European Patent Application No. 116,784, published Aug. 29, 1984. The human analog of the 28 amino acid Cardionatrin I having a met[12] replacement of atrial peptides thus would provide significant advantages in the use of these peptides. Several peptidase inhibitors which have been suggested heretofore as useful in preventing enzymic degradation of the atrial peptides are bestatin, an aminopeptidase inhibitor; SQ 20881, a carboxypeptidase inhibitor; and aprotinin, an inhibitor of serine protease. See Tang et al., supra, and Thibault et al., supra.

BRIEF DESCRIPTION OF THE INVENTION

In accordance with the present invention it has been found surprisingly that the bioactivity of small atrial peptides can be prolonged or enhanced by the substantially contemporaneous administration of thiorphan or kelatorphan.

These small atrial peptides can be represented by the following amino acid sequence:

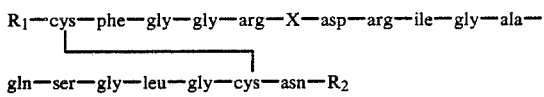

wherein
$R_1$ = H; ser; ser-ser; arg-ser-ser; arg-arg-ser-ser; leu-arg-arg-ser-ser; ser-leu-arg-arg-ser-ser;
$R_2$ = OH; ser; ser-phe; ser-phe-arg; ser-phe-arg-tyr;
X = ile; met;
or the physiologically acceptable salts, esters or amides thereof.

A preferred atrial peptide for use in the method of the invention is atriopeptin III (AP-III) as defined above. Illustrative salt derivatives of the atrial peptides are, for example, the acid salts such as the HCl salt. Esters and amides are illustrated, for example, by the carboxy methyl or ethyl esters and the carboxy amide form of the atrial peptide.

Thiorphan and kelatorphan are known compounds which have been reported heretofore to have enkephalinase inhibitor activity. These compounds have not been reported heretofore to have been used in conjunction with atrial peptides or to have the property of prolonging or enhancing the bioactivity of atrial peptides.

Thiorphan, first reported by Roques et al., *Nature* 288, 286–288 (1980), is the generic name for N-(DL-2-benzyl-3-mercapto-propionyl)glycine. It can be represented by the following chemical structure:

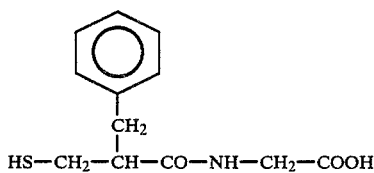

The above structurally represented compound can exist as a racemic mixture of R and S isomers. Either of these isomers or mixtures thereof can be used herein.

Kelatorphan, first reported by Bouboutou, *Life Sci.* 35, 1023–1030 (1984), is the generic name for [(R)-3-(N-hydroxy)carboxamido-2-benzylpropanoyl]-L-alanine. Alternative chemical nomenclature is N-[3(R)-[(hydroxyamino)carbonyl]-2-benzyl-1-oxopropyl]-L-alanine, as reported by Fournié-Zaluski et al., *J. Med. Chem.* 28, 1158–1169 (1985). Kelatorphan can be represented by the following chemical structure:

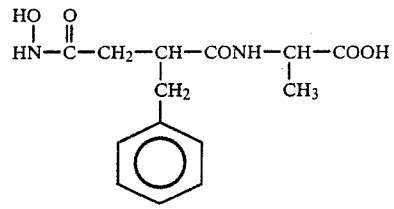

The above structurally represented compound can exist as a diasteroisomeric mixture of RS and SS isomers. Either of these isomers or mixtures thereof can be used herein.

DETAILED DESCRIPTION OF THE INVENTION

The compounds used in the method of the invention can be made by well-known conventional procedures. Thus, the small atrial peptides can be synthetically prepared by conventional solid phase methods of peptide synthesis. For general description of such procedures, see Merrifield, *J. Amer. Chem. Soc.* 85, 2149–54 (1963) and *Science* 150, 178–85 (1965); Stewart and Young, "Solid Phase Peptide Synthesis," W. H. Freeman and Company, San Francisco, 1969; the review article by Merrifield in *Adv. Enzymol.* 32, 291–296, F. F. Nold, Ed., Interscience Publ., New York, 1969; and Erickson and Merrifield, *The Proteins*, Vol. 2, 255, Neurath and Hall, Eds., Academic Press, New York, 1976.

Some of these small peptides also are available commercially from supply houses, e.g. Peninsula Labs, Belmont, Calif.

Thiorphan can be prepared by conventional peptidic condensation reaction between two suitably protected residues. For example, the functional groups (i.e., amino, carboxy, mercapto) which are not involved in the reaction by the formation of the peptide linkage (i.e., —CONH) during the condensation reaction may be protected with one or more conventional protecting groups prior to the condensation reaction. A typical such example for the preparation of thiorphan is described in U.S. Pat. No. 4,513,009, Example 20. Thiorphan also is available commercially from Peninsula Laboratories, Inc., Belmont, Calif.

Kelatorphan can similarly be prepared by conventional peptidic condensation reactions between two suitably protected residues. Typical such examples of preparation are described by Fournié-Zaluski et al., *J. Med. Chem.* 28, 1158–1169 (1985), compound 13, and in European Patent Application No. 82,088, published June 22, 1983.

Although specific methods of preparing the compounds used in the method of the invention are described herein it will be appreciated that the invention is not limited to any particular method of preparation.

The use of thiorphan and kelatorphan to prolong or enhance the bioactivity of small atrial peptides is demonstrated herein in vitro and in vivo.

In vitro, the enhancement of bioactivity is illustratively shown in a rabbit kidney brush border membrane preparation. For example, it was found that atriopeptin III (AP-III) was proteolytically degraded by incubation in this preparation with a consequent loss of active material. However, the bioactivity of the AP-III was substantially prolonged or enhanced by the presence of nanomolar concentrations of thiorphan or kelatorphan.

In vivo, the enhancement of bioactivity is illustratively shown in standard laboratory experimental rats. It was found that AP-III levels upon intravenous infusion were increased at least two-fold by the contemporaneous infusion of thiorphan in amounts ranging from 1–30 mg/kg of body weight.

The contemporaneous administration can be coinfusion of the atrial peptide and the thiorphan or kelatorphan inhibitor, or the inhibitor can be separately administered shortly before or after the atrial peptide administration. Preferably, the inhibitor would be administered prior to or at the same time as the atrial peptide administration to maximize its inhibitory effect since it is known that the atrial peptides are rapidly metabolized. The proportion of inhibitor to be administered illustratively can be about nanomolar or greater relative to the micromolar amount of the atrial peptide administered, although it should be understood that the invention is not limited to such proportions.

The atrial peptide can be administered as a diuretic, natriuretic, vasodilator, smooth muscle relaxant, and hypotensive agent to patients in need of such treatments. The amount of peptide which would normally be administered is primarily dependent upon the physical characteristics of the recipient and the severity of the pathological condition to be treated. The amount to be administered must be an effective amount, that is, an amount which is medically beneficial but does not present toxic effects which overweigh the advantages which accompany its use. The preferable route is parenteral, especially intravenous. Intravenous administration of the peptide in solution with normal physiologic saline is illustrative. Other suitable formulations of the active peptide in pharmaceutically acceptable diluents or carriers in therapeutic dosage form can be prepared by reference to general texts in the pharmaceutical field such as, for example, Remington's Pharmaceutical Sciences, Ed. Arthur Osol, 16th ed., 1980, Mack Publishing Co., Easton, Pa. Intranasal administration of the atrial peptide such as described in copending application Ser. No. 732,781, filed May 10, 1985, and assigned to a common assignee, also is suitable. The disclosure of said application is incorporated herein by reference.

The following examples will further illustrate the invention although it will be understood that the invention is not limited to these specific examples.

EXAMPLE 1

The biological activity of several small atrial peptides was tested by measuring the vasorelaxation of norepinephrine-contracted rabbit aorta essentially by the assay method of Currie et al., Science 221, 71–73(1983). According to this bioassay, spiral strips of rabbit thoracic aorta are continuously perfused with oxygenated Krebs-Henseleit solution at 37° C. and maintained in tone by continuous infusion of norepinephrine at $4.5 \times 10^{-8}$ M concentration. The effects of the test peptides are then determined by application of the test peptide in buffered saline solution with micropipets to the stream of medium flowing over the aorta tissues. The relaxation in mm of the treated strip is measured after a given period of time, for example 30 minutes, and compared against a control standard.

In order to test the effect of thiorphan and kelatorphan on the bioactivity of the atrial peptide, the test peptides were preincubated with a rabbit kidney brush border membrane preparation with or without additional nanomolar concentrations of the thiorphan or kelatorphan. The thiorphan was purchased from Peninsula Laboratories, Inc., Belmont, Calif. The kelatorphan was prepared according to the method described for compound 13 by Fournié-Saluski et al., J. Med. Chem. 28, 1158–1169 (1985).

Preparation of rabbit kidney brush border membranes

The following procedure was performed at 4° C. Rabbit kidneys were obtained fresh and were perfused with buffer A (containing 5 mM Tris, pH 7.5, 0.25 M sucrose, 3 mM $MgCl_2$ and 1 mM EDTA) to remove the blood. (EDTA=ethylenediaminetetraacetic acid.) The kidneys were minced, homogenized in 5 volumes of ice-cold buffer A with a Brinkmann Polytron homogenizer and filtered through two layers of cheesecloth. The filtrate was centrifuged at $5,000 \times g$ for 20 min, the pellet was discarded and the supernatant was centrifuged at $15,000 \times g$ for 20 min. The supernatant was retained and then centrifuged at $100,000 \times g$ for 90 min. The pellet was resuspended in 50 mM Tris, pH 7.5, and the suspension was centrifuged at $100,000 \times g$ for 90 min. The washed pellet was resuspended in 50 mM Tris, pH 7.5, to give a final protein concentration of 4 mg/ml using the protein assay of Bradford, Anal. Biochem. 72, 248–254 (1976). The membrane preparation was assayed for aminopeptidase and alkaline phosphatase activities which are the marker enzymes for the kidney brush border. See Inui et al., Biochim. Biophys. Acta 647, 150–154 (1981). The final membrane preparation was enriched 8-fold in alkaline phosphatase activity, and 11-fold in aminopeptidase activity, compared to the homogenate.

Inhibition of AP bioinactivation

Renal brush border membranes (10–20 μg) were preincubated for 15 min at 25° C. in a solution containing the inhibitor and 50 mM Tris, pH 7.5. The incubation reaction was initiated by the addition of 40 μM atrial peptide [AP-III, AP-I or SLRR(Met$^8$)-AP-III] in a final volume of 0.5 ml. Incubations were for 60 min at 25° C. and were terminated by removing the membranes by filtration using Gelman GA-6 filters. The filtrates were immediately frozen on dry ice and were stable for 1 week when stored at −80° C. Samples containing the peptide degradation products were resolved by $C_{18}$ reversed phase high pressure liquid chromatography (HPLC). The frozen samples were thawed immediately before injection onto a Vydac $C_{18}$ column (4.6 mm I.D.×25 cm; 5 micron/300 Å) equilibrated with water containing 0.05% trifluoracetic acid (TFA). Peptide fragments and starting material were separated on a linear gradient of 0–35% acetonitrile also containing 0.05% TFA. Both the gradient and the flow rate (1 ml/min) were maintained by a Waters HPLC system consisting of two Model 510 pumps connected to an Automated Gradient Controller. Column effluent was monitored at 220 nm by a Waters Model 481 spectrophotometer, and the amount of atrial peptide material and peptide fragments were measured via a Hewlett-Packard Model 3392A integrator.

Table 1 below sets forth the results of the above tests. It is seen that AP-III, AP-I, and SLRR(Met$^8$)AP-III were degraded by the proteolytic activity of renal brush border membranes. One of the peptide fragments generated during the 60 min incubation, des Ser$^1$-AP, was shown to have the same vasorelaxant activity as the intact atrial peptide by the rabbit aorta relaxation test described hereinbefore. Therefore, in those cases where the N-terminal serine was removed, the total amount of biologically active material remaining at the end of the incubation was taken as the % starting material remaining plus % des $Ser^1$-AP-I or des $Ser^1$-AP-III (as appropriate), as calculated from the peak areas of the individual peptides on HPLC.

Table 1 shows that low concentrations of thiorphan and two stereoisomers (R,S and S,S) of kelatorphan inhibit the loss of atrial peptide bioactivity during incubation with renal brush border membranes.

TABLE 1

Inhibition by thiorphan, and (R,S) and (S,S) kelatorphans of atrial peptide bioinactivation by rabbit kidney brush border membranes (RBBM). Incubations were for 60 min at 25° C. in a total volume of 0.5 ml 50 mM Tris, pH 7.5, containing (a) 40 μM atrial peptide, (b) 40 μM atrial peptide and 20 μg RBBM, and (c) 40 μM atrial peptide, 20 μg RBBM and 100 nM inhibitor.

| | Peak Areas as % Initial AP | | |
|---|---|---|---|
| | AP | des $Ser^1$-AP | AP + des $Ser^1$-AP |
| 1. (a) AP-I. | 100 | 0 | 100 |
| (b) AP-I, RBBM, | 0 | 0 | 0 |
| (c) AP-I, RBBM, thiorphan. | 27.3 | 60.6 | 87.9 |
| 2. (a) AP-III. | 100 | 0 | 100 |
| (b) AP-III, RBBM | 3.3 | 2.6 | 5.9 |
| (c) AP-III, RBBM, thiorphan. | 38.1 | 48.0 | 86.1 |
| 3. (a) SLRR($Met^8$)AP-III. | 100 | 0 | 100 |
| (b) SLRR($Met^8$)AP-III, RBBM. | 0 | 0 | 0 |
| (c) SLRR($Met^8$)AP-III, RBBM, thiorphan. | 86.5 | 0 | 86.5 |
| 4. (a) AP-III. | 100 | 0 | 100 |
| (b) AP-III, RBBM. | 3.3 | 2.6 | 5.9 |
| (c) AP-III, RBBM, (R,S) kelatorphan. | 16.5 | 14.9 | 31.4 |
| 5. (a) AP-III. | 100 | 0 | 100 |
| (b) AP-III, RBBM. | 2.1 | 8.8 | 10.9 |
| (c) AP-III, RBBM, (S,S) kelatorphan. | 17.2 | 32.1 | 49.3 |

EXAMPLE 2

Plasma levels of atriopeptin III (AP-III) were tested in rats in which the AP-III was infused intravenously both with and without contemporaneous administration of thiorphan.

Male Sprague-Dawley rats, 240–310 g, were used for all tests. The rats were housed in the test facilities for at least 6 days before they were used.

Cannulas were made of PE-10 (polyethylene) tubing inserted and glued into a piece of PE-50 tubing. Rats were anesthetized with pentobarbital (50 mg/kg i.p.) and had cannulas inserted into the left femoral vein and artery. Both were inserted four cm into the vessels and tied securely. They were then tunnelled under the skin and brought out between the rat's shoulder blades and then cut so that only 1–2 cm was externalized. Cannulas were glued in place using Superglue and filled with saline containing 100 units heparin/ml. Rats were allowed to wake up and then housed individually with food and water ad libitum.

Two days after surgery, the rats were weighed and put into restraining cages that allowed limited movement. AP-III was dissolved in 5% dextrose/0.225% saline for infusion into the femoral vein; the rate of the solute infusion was 1.25 ml/hr/rat. Blood was collected from the femoral artery and replaced with saline containing 10 units heparin/ml. In most tests, 0.3 ml blood was taken, except that when basal AP-III levels were measured 0.4 ml blood was withdrawn. Blood was immediately centrifuged in a microcentrifuge for one minute and plasma was frozen in plastic tubes placed on dry ice. Samples were kept in a −80° C. freezer until they were analyzed.

Thiorphan was dissolved in a minimal amount of 0.1 N NaOH to produce the sodium salt. The solution was immediately neutralized using 0.5 N HCl and diluted to a final concentration with 0.9% saline. HPLC analysis showed no apparent degradation due to this method of dissolution.

In the first test, AP-III was infused at a rate of 833 ng/min/kg i.v. Blood samples were taken 20 and 30 minutes after the start of the AP-III infusion to show that a steady state plasma concentration had been obtained. After taking the second sample, thiorphan was given as a bolus injection into the femoral artery and the line was flushed with 0.2 ml saline. The doses of thiorphan were 1,3,10 and 30 mg/kg; one set of rats received only a saline bolus as a control. Blood was taken 10,20,30 and 60 minutes after the injection of thiorphan. AP-III was infused during the entire experiment for a total of 90 minutes.

In the second test, the level of thiorphan was kept constant at 3 mg/kg and the rate of AP-III infusion was varied. AP-III was infused into the femoral vein for a total of 60 minutes at a rate of 150,450 and 900 ng/kg/min; another group of rats received only an infusion of dextrose/saline to determine if thiorphan affected the basal levels of AP-III. Blood was taken at 15 and 30 minutes after the start of the AP-III infusion to check for a steady state AP-III plasma concentration. After the 30 min sample, thiorphan (3 mg/kg) was injected arterially and additional blood samples were taken 15 and 30 min later (45 and 60 minutes after the start of the AP-III infusion).

Plasma AP-III levels were analyzed by radioimmunoassay using a second antibody to separate free and bound AP-III. The label was $^{125}$I-AP-III that was purified by HPLC after iodination. Conditions were set so that 35–40% of the total counts were precipitated. The incubation medium contained sodium phosphate, pH 7.4, 0.25% bovine serum albumin (BSA), 0.5% sodium azide and 3% PEG-8000 (polyethylene glycol). The primary antibody was from a guinea pig immunized against AP-III. The incubations were done overnight at 6° C. The next day, 2 ml of 0.125% BSA was added to each tube and then they were centrifuged for 45 min at 3000 rpm. They were decanted and the radioactivity was counted in a Micromedic gamma counter. The standard curve contained 10 to 600 pg AP-III/tube. Only the linear portion of the curve was used for quantification. Plasma samples were diluted so that the AP-III concentrations were in the range of the standard curve.

Tables 2 and 3 set forth the results of the above tests. In the first test during the infusion of AP-III at a rate of 833 ng/kg/min, it is seen in Table 2 that the plasma AP-III concentrations were stable at 9–11 ng/ml. Ten minutes after injecting thiorphan, the levels increased at least 2-fold and at later times 3-fold over control levels. In control rats receiving only AP-III and no thiorphan, plasma AP-III levels remained constant at 11–12 ng/ml. Using analysis of variance, the plasma AP-III concentrations are statistically different from control levels at all time points after thiorphan at doses of 3,10 and 30 mg/kg and at all but the last point for 1 mg/kg.

In the second test (Table 3), the dose of thiorphan was kept constant at 3 mg/kg and was also given 30 min. after the start of various infusion rates of AP-III.

Plasma concentrations of AP-III were constant before the injection of thiorphan. Levels increased 2–3 fold after thiorphan administration. When the inhibitor was given to rats receiving no exogenous peptide, basal levels of AP-III did not increase.

TABLE 2

Plasma AP-III Concentration Before and After Injection of Thiorphan with Continuous Infusion of AP-III

| Dose Thiorphan (mg/kg) | AP-III Plasma concn. (ng/ml)[a] | | | | | |
|---|---|---|---|---|---|---|
| | 20 min | 30 min | 40 min | 50 min | 60 min | 90 min |
| 0 (n = 4)[b] | 9.6 ± 1.6 | 10.8 ± 1.1 | 11.2 ± 1.3 | 11.3 ± 1.1 | 11.7 ± 0.7 | 10.6 ± 1.4 |
| 1 (n = 3) | 9.2 ± 2.4 | 9.7 ± 1.0 | 23.2 ± 3.1 | 22.2 ± 3.9 | 18.7 ± 2.2 | 15.3 ± 3.9 |
| 3 (n = 4) | 10.1 ± 1.6 | 11.0 ± 1.1 | 26.7 ± 3.5 | 29.5 ± 4.0 | 28.9 ± 5.6 | 21.2 ± 3.9 |
| 10 (n = 5) | 9.7 ± 2.4 | 10.6 ± 2.9 | 24.7 ± 2.7 | 29.2 ± 3.1 | 30.2 ± 4.8 | 25.5 ± 5.5 |
| 30 (n = 4) | 9.2 ± 1.1 | 8.8 ± 1.0 | 22.5 ± 2.7 | 28.8 ± 5.6 | 30.7 ± 6.0 | 31.3 ± 7.8 |

[a]Values are Mean ± S.D. Times are minutes after the start of coinfusion of AP-III. Thiorphan was given after the 30 min blood sample was taken.
[b]Number of animals/group.

TABLE 3

Plasma Concn. of AP-III after Varying the Infusion Rate of AP-III With a Constant Dose of Thiorphan (3 mg/kg)

| Infusion Rate AP-III (ng/kg/min) | Plasma AP-III concn. (ng/ml)[a] | | | |
|---|---|---|---|---|
| | 15 min | 30 min | 45 min | 60 min |
| 0 (n = 5)[b] | 0.4 ± 0.2 | 0.6 ± 0.3 | 0.6 ± 0.3 | 0.5 ± 0.2 |
| 150 (n = 5) | 0.9 ± 0.2 | 1.0 ± 0.6 | 2.6 ± 0.8 | 3.3 ± 1.7 |
| 450 (n = 4) | 4.2 ± 1.0 | 4.5 ± 1.2 | 11.2 ± 3.6 | 12.8 ± 5.8 |
| 900 (n = 4) | 11.2 ± 3.5 | 13.6 ± 1.8 | 29.8 ± 7.6 | 23.0 ± 6.0 |

[a]Values are Mean ± S.D. Thiorphan was given after the 30 minute sample was taken.
[b]Number of animals/group.

Various other examples will be apparent to the person skilled in the art after reading the foregoing specification without departing from the spirit and scope of the invention. It is intended that all such other examples be included in the scope of the appended claims.

What is claimed is:

1. The method of prolonging or enhancing the bioactivity of an atrial peptide administered to a mammal comprising substantially contemporaneously administering to said mammal an effective amount of thiorphan or kelatorphan.

2. The method of claim 1 in which the atrial peptide has the following amino acid sequence

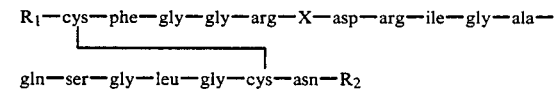
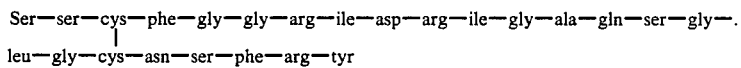

wherein $R_1$=H; ser; ser-ser; arg-ser-ser; arg-arg-ser-ser; leu-arg-arg-ser-ser; ser-leu-arg-arg-ser-ser;

$R_2$=OH; ser; ser-phe; ser-phe-arg; ser-phe-arg-tyr;

X=ile; met;

or the physiologically acceptable salts, esters or amides thereof.

3. The method of claim 1 in which the atrial peptide has the following amino acid sequence Ser—ser—cys—phe—gly—gly—arg—ile—asp—arg—ile—gly—ala—gln—ser—gly—.
leu—gly—cys—asn—ser—phe—arg—tyr 4. The method of claim 1 in which the atrial peptide is administered with thiorphan.

5. The method of claim 1 in which the atrial peptide is administered with kelatorphan.

* * * * *